(12) United States Patent
Guldalian

(10) Patent No.: US 8,262,595 B2
(45) Date of Patent: Sep. 11, 2012

(54) MUSCULOSKELETAL SUPPORT SYSTEM

(75) Inventor: Eric L. Guldalian, West Trenton, NJ (US)

(73) Assignee: Neurotron Medical Inc., West Trenton, NJ (US)

( * ) Notice: Subject to any disclaimer, the term of this patent is extended or adjusted under 35 U.S.C. 154(b) by 1 day.

(21) Appl. No.: 12/853,165

(22) Filed: Aug. 9, 2010

(65) Prior Publication Data

US 2011/0034842 A1  Feb. 10, 2011

Related U.S. Application Data

(60) Provisional application No. 61/232,743, filed on Aug. 10, 2009.

(51) Int. Cl.
  *A61F 5/00* (2006.01)
(52) U.S. Cl. ............................................. 602/13; 602/19
(58) Field of Classification Search ............... 602/13, 602/19; 128/869, 876, DIG. 20; 2/2, 338
  See application file for complete search history.

(56) References Cited

U.S. PATENT DOCUMENTS

| | | | |
|---|---|---|---|
| 4,135,503 A * | 1/1979 | Romano | 602/13 |
| 4,682,588 A * | 7/1987 | Curlee | 602/13 |
| 5,062,414 A | 11/1991 | Grim | |
| 5,195,948 A * | 3/1993 | Hill et al. | 602/19 |
| 5,205,814 A | 4/1993 | Lundrigan et al. | |
| 5,396,906 A | 3/1995 | Harrold | |
| 5,450,858 A * | 9/1995 | Zablotsky et al. | 128/876 |
| 5,626,557 A | 5/1997 | Mann | |
| 5,628,721 A | 5/1997 | Arnold et al. | |
| 5,643,185 A | 7/1997 | Watson et al. | |
| 6,331,170 B1 | 12/2001 | Ordway | |
| 6,820,783 B2 | 11/2004 | Baele | |

* cited by examiner

*Primary Examiner* — Michael A. Brown

(74) *Attorney, Agent, or Firm* — Muskin & Cusick LLC

(57) ABSTRACT

A removable air bladder, juxtaposed between support materials, expands or contracts within special voids of orthosis devices. An orthosis system comprise one or more removable air bladders placed on one support material or juxtaposed between two support materials, each of the air bladders being disposed to inflate and deflate by storing and releasing a gas through an airline having a release valve. A pump may be operatively connected to the air line for pumping gas into the air bladder. A pressure sensor may be disposed adjacent to the air bladder to measure pressure of the air bladder against one of the support materials to determine when the pump should be powered on or off. At least one expansion limiter straps may be disposed to control a maximum distance the support materials can be moved apart when the air bladder is inflated.

17 Claims, 4 Drawing Sheets ary Patent Application No. 61/232,743, filed Aug. 10,

MUSCULOSKELETAL SUPPORT SYSTEM

CROSS-REFERENCE TO RELATED APPLICATIONS

This application claims the benefit of priority to U.S. Provisional Patent Application No. 61/232,743, filed Aug. 10, 2009, herein incorporated by reference in its entirety.

BACKGROUND OF THE INVENTION

The present invention relates to a musculoskeletal support system and, more particularly, to a removal air bladder juxtaposed between support materials that may expand or contract within spatial voids of orthosis devices.

Conventional orthosis devices that integrate an air bladder are permanently fixed and/or do not apply directional pressure towards the body from behind a rigid or semi-rigid material. In order to expand or contract, air bladders are designed to be soft, flexible and pliable. Conventional devices integrate air bladders in orthosis devices that are permanently fastened and/or have direct contact with the body, which does not allow a rigid support level to be achieved. The prior art includes a removable air bladder placed in a pocket or pouch made of a fabric material that rests against the body as found in U.S. Pat. No. 5,626,557 (Mann), U.S. Pat. No. 6,331,170 (Ordway), and U.S. Pat. No. 6,820,783 (Beale). The prior art also includes an air bladder permanently positioned in between two or more layers of natural or synthetic non-rigid material that has direct contact with the body as found in U.S. Pat. No. 5,195,948 (Hill), U.S. Pat. No. 5,205,814 (Lundrigan), U.S. Pat. No. 5,396,906 (Harrold), and U.S. Pat. No. 5,643,185 (Watson). Another example of the prior art includes a permanently fixed air bladder behind a gel filled pad that has direct contact with the body as found in U.S. Pat. No. 5,062,414 (Grim) and U.S. Pat. No. 5,628,721 (Arnold).

As can be seen, there is a need for a removable assembly that may include an air bladder that may expand outward directly against rigid and/or semi-rigid material that provides firm support when placed against the body.

SUMMARY OF THE INVENTION

In one aspect of the present invention, a spatial rectifier comprises at least one flexible support material; at least one bladder adjacent to the at least one support material; at least one limiter strap to limit expansion of the at least one bladder; and an air line connected to the at least one bladder, the air line adapted to be connected to an air pump.

In another aspect of the present invention, a spatial rectifier for filling a void between an orthotic and a user, comprises a first and a second flexible support material; at least one bladder sandwiched between the first and second flexible support materials; at least two limiter straps adapted to limit expansion of the at least one bladder; an air line connected to the at least one bladder, the air line adapted to be connected to an air pump; and a wire harness connected to at least one transducer positioned between the bladder and one of the first and second flexible support materials.

In a further aspect of the present invention, a spatial rectifier for filling a void between an orthotic and a user, comprises a first and a second flexible support material; at least one bladder sandwiched between the first and second flexible support materials; at least two limiter straps adapted to limit expansion of the at least one bladder; and an air line connected to the at least one bladder, the air line adapted to be connected to an air pump, wherein the first support material is adapted to be positioned between the orthotic and the bladder; the second support material is adapted to be positioned between the bladder and the user; and the second support material is more flexible than the first support material.

These and other features, aspects and advantages of the present invention will become better understood with reference to the following drawings, description and claims.

DETAILED DESCRIPTION OF THE INVENTION

Figure 1:
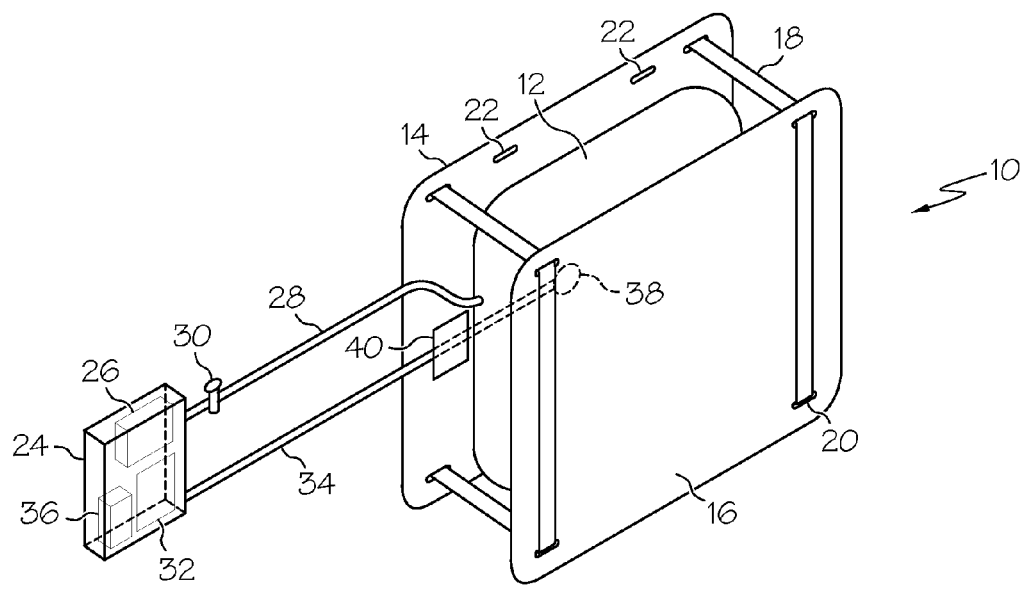
FIG. 1 is a perspective view of a support system according to an embodiment of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, an embodiment of the present invention provides a removable air bladder, juxtaposed between support materials, that expands or contracts within spatial voids of orthosis devices. An exemplary embodiment of the present invention includes an orthosis system comprising one or more removable air bladders placed on one support material or juxtaposed between two support materials, each of the air bladders being disposed to inflate and deflate by storing and releasing a gas through an airline having a release valve. A pump may be operatively connected to the air line for pumping gas into the air bladder. A pressure sensor may be disposed adjacent to the air bladder to measure pressure of the air bladder against one of the support materials to determine when the pump should be powered on or off. At least one expansion limiter straps may be disposed to control a maximum distance the support materials can be moved apart when the air bladder is inflated.

When an orthosis device is worn or applied with a loose fit, spatial voids can form in or around the treatment area, thereby reducing the clinical efficacy of the orthosis device. Individuals who wear such products often have a medical condition that either prevents or limits their ability to pull opposing sides of a brace together so a tight or snug fit can be achieved. This can be due in part to the physical inability to properly extend an arm while pulling a cord or strap that tightens the fit of a brace, or to the physical inability to stretch and hold one end of a brace over the opposite side until fasteners become fully engaged.

Referring to FIGS. 1, 3 and 6-8, a removable spatial rectifier for orthosis devices 10 may include one or more bladders 12 disposed between a first support material 14 and a second support material 16. In one embodiment, the bladder 12 may float freely between the first and second support materials 14, 16. Alternatively, the air bladder 12 may be fastened to one or both of the first and second support materials 14, 16 using, for example, a liquid adhesive 46 (see FIG. 8), a double-sided adhesive tape, or the like. Typically, the connection points for the bladder 12 and the first and/or second support material 14, 16 may be the horizontal and vertical center points on each of the facing sides of the bladder 12. Alternatively, the bladder 12 can be detached from one or both of the support materials 14, 16, attached to both support materials 14, 16, or a hook and loop fastener can be used to vary the connection from the center point. In one embodiment of the present invention, during use thereof, the first support material 14 may be positioned against an orthotic (not shown) and the second support material 16 may positioned against the wearer.

The dimensions of the air bladder 12 may vary in height, width and depth. The depth of a deflated air bladder 12 will be different from the depth of an inflated air bladder 12. An inflated air bladder 12 can have dimensions, such as height, width and depth, which dynamically change during the inflation and deflation process.

The first and second support materials 14, 16 may be formed of a rigid, yet flexible material such as, for example, a flexible plastic. In one embodiment, the second support material 16 may have a greater flexibility than the first support material 14. In this configuration, the support material between the bladder and the orthotic (first support material 14) may be more rigid, whereas the support material pushing toward the patient (second support material 16) may be more flexible. The first and second support materials 14, 16 may be curvilinear shaped and may be made in different sizes and contours depending on application. In one embodiment, the first and second support materials 14, 16 may have the same shape and size. The first and second support materials 14, 16 may have a thickness between about 0.125 inch to about 0.0625 inch.

Limiter straps 18 may be used to limit the maximum separation distance between the first support material 14 and the second support material 16 when the bladder 12 is inflated. The limiter straps 18 may be formed of a flexible, non-stretchable material that can be individually adjusted with strap locks 42 (see FIG. 3). The limiter straps 18 may be two limiter straps passing through slots 20 cut into corners of each of the first and second support materials 14, 16. The slots 20 may be positioned in various locations of the first and second support materials 14, 16 and the slots 20 may have sufficient size for the limiter straps 18 to pass there through. Alternatively, the limiter straps 18 may be made from a flexible strap permanently fixed to one, both or neither of the first and second support materials 14, 16 at two or more locations using fasteners such as adhesive, screws, rivets, studs, strap locks and/or a hook and loop fastener.

The spatial rectifier 10 may include slots 22 cut into the first support material 14. These slots 22 may be used to secure the spatial rectifier 10 to an orthotic (not shown) using optional straps or belting (not shown).

An electronic enclosure 24 may house an electromechanical pump 26. The pump 26 may be used to deliver a gas, such as air, to the bladder 12, via an air line 28. A release valve 30 may be disposed in the air line 28 to release air from the bladder 12. The release valve 30 may be a conventional valve to fluidly communicate the inside of the air line 28 to ambient air, such as a screw valve. In an alternate embodiment, the release valve 30 may be mounted on the electronic enclosure 24.

The electronic enclosure 24 may further include electronic circuitry 32 on a printed circuit board (PCB, not shown) with a microcontroller and other components. The electronic circuitry 32 may interact with the pump 26 and an input transducer, such as a pressure sensor 38, via a wire harness 34. For example, during use of the spatial rectifier 10, the pressure sensor 38 may detect insufficient pressure (as predetermined by, for example, the patient, the type of orthotic, the location of the void being filled, and the like) and may send a signal to the pump 26 to add air to the bladder 12. The pressure sensor 38 may be located between the bladder 12 and either of the first or second support materials 14, 16. In one embodiment, two pressure sensors 16 may be used, with one between the bladder 12 and the first support material 14 and the other between the bladder 12 and the second support material 16. A power supply, such as a battery pack 36, may be disposed within the electronic enclosure 24. The battery pack 36 may provide power to the electronic circuitry 32 and the pump 26.

The wire harness 34 and the air line 28 may be of sufficient length to permit a wearer to have access to the electronic enclosure 24. In one embodiment, the wire harness 34 and the air line 28 may be secured to each other or bundled together in a single tube or wrap to limit the number of separate connections between the electronic enclosure 24 and the first and second support materials 14, 16. The wire harness 34 and/or the air line 28 may be connected to one of the first or second support materials 14, 16. In one embodiment, an adhesive 40 may be used to attach the wire harness 34 to the first support material 14.

Figure 2:
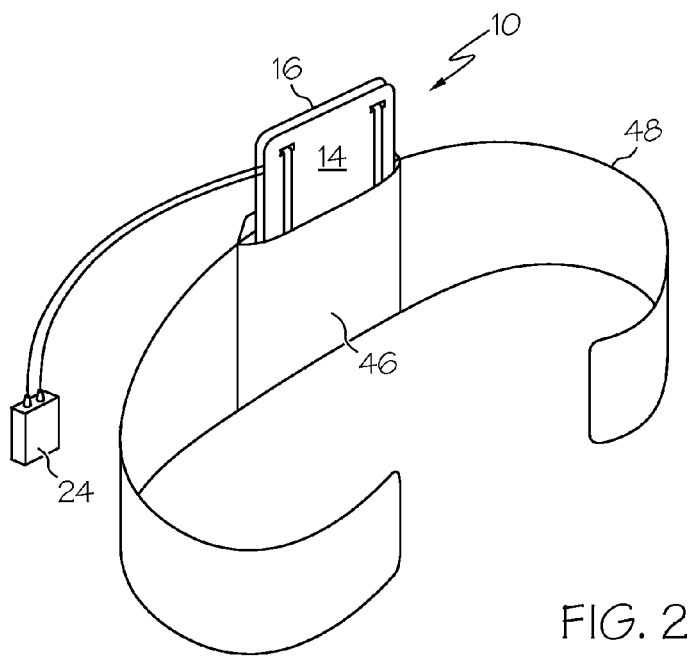
FIG. 2 is a perspective view of the support system of FIG. 1 installed in an orthotic brace.
Figure 3:
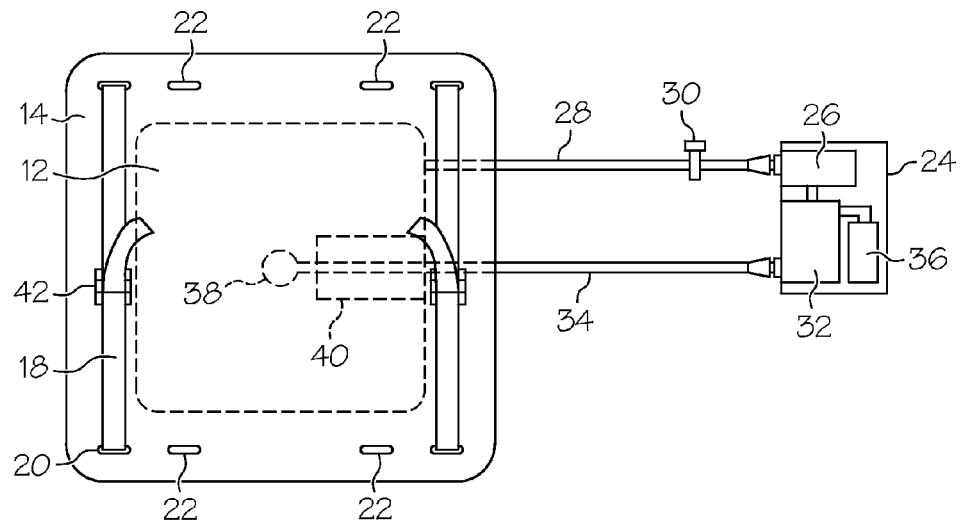
FIG. 3 is an exterior view of the support system of FIG. 1.

Referring to FIG. 2, the spatial rectifier 10 may be positioned in a pouch 46 formed in an orthotic brace 48. The orthotic brace 48 may be, for example, a lumbosacral orthotic.

Figure 4:
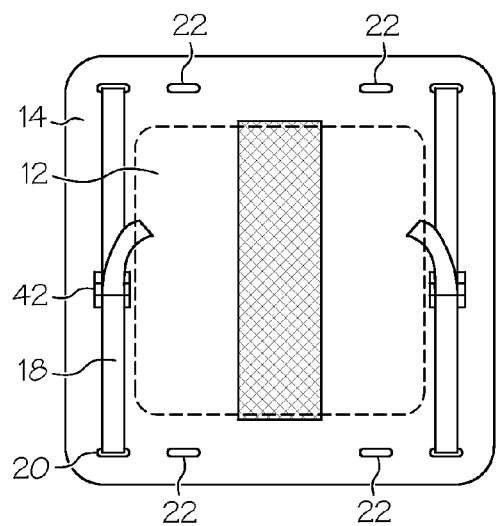
FIG. 4 is an exterior view of a support system according to another embodiment of the present invention.

Referring to FIG. 4, the spatial rectifier 10 of FIG. 1 may be configured with a hook and loop fastener 44, such as Velcro®, that may be attached to the first support material 14. The fastener 44 may secure with a mating hook and loop fastener in an orthotic (not shown). The fastener 44 may help secure the spatial rectifier 10 to the orthotic.

Figure 5:
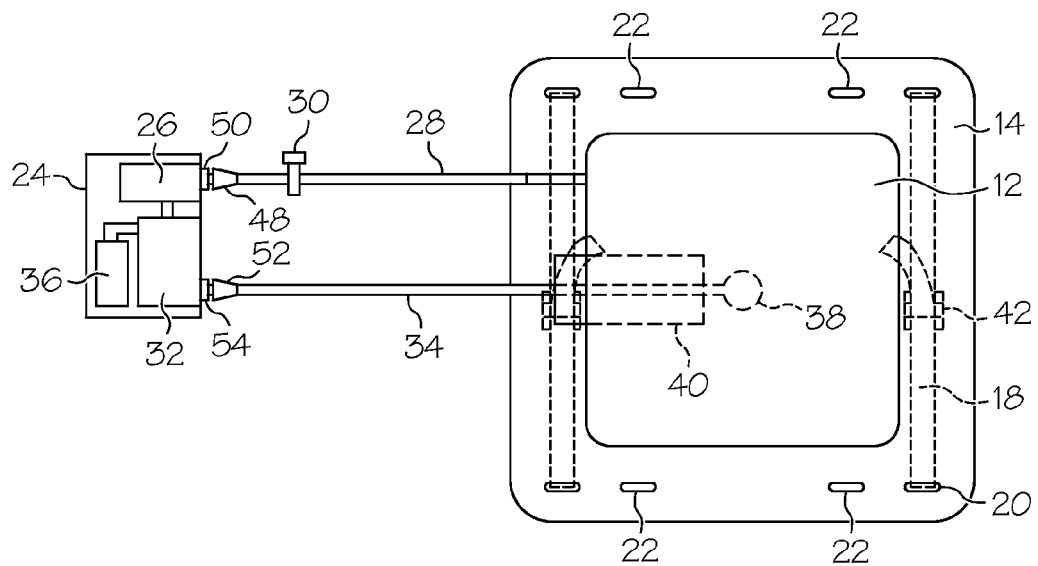
FIG. 5 is an interior view of a support system according to another embodiment of the present invention.
Figure 6:
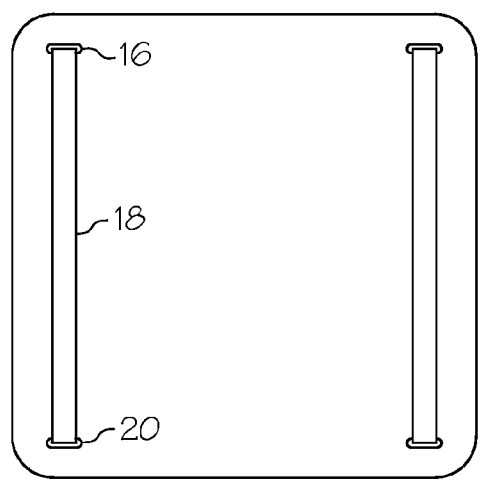
FIG. 6 is a an exterior view of the support system of FIG. 1.
Figure 7:
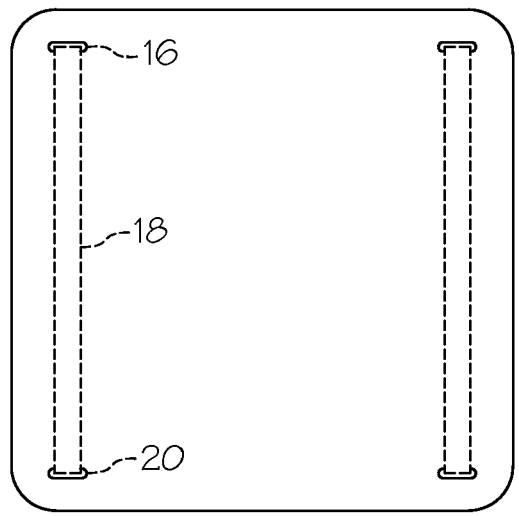
FIG. 7 is an interior view of the support system of FIG. 1.
Figure 8:
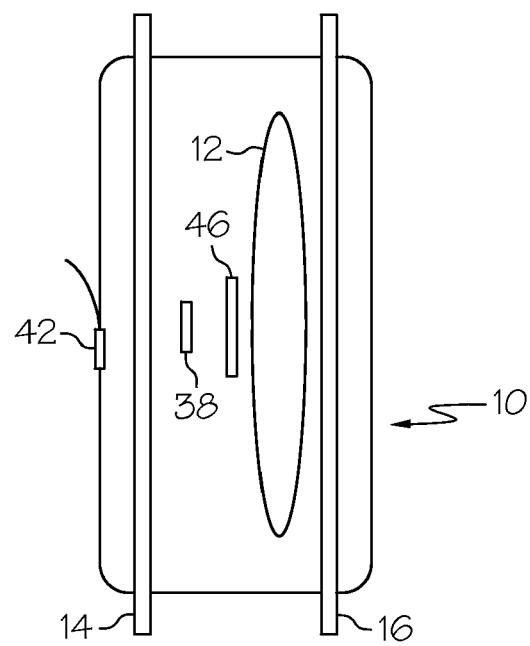
FIG. 8 is a sectional view of the support system of FIG. 1.

Referring to FIG. 5, the air line 28 may have a coupling 48 at the end thereof. The coupling 48 may connect with another coupling 50 in the electronic housing 24. The couplings 48, 50 may form an air-tight connection. The connection between the couplings 48, 50 may be releasable by known means, such as by a quick release mechanism. When the air line 28 is disconnected from the electronic housing 24, a hand pump (not shown) may be connected to the air line 28 to permit manual inflation of the bladder 12. The wire harness 34 may terminate with a cable plug 52. The cable plug 52 may electrically connect to a wire cable jack 54 in the electronic housing 24. The plug 52 and jack 54 may be separable to allow the electronic housing 24 to be disconnected from the wire harness 34.

The air bladder 12, air line 28 and hand pump (not shown) are typically made from non-latex materials, such as polychloroprene. As discussed above, the first and second support materials 14, 16 may be made of a flexible plastic. The remaining components may be made of suitable conventional materials.

An accelerometer (not shown) can be added to determine the angle of tilt during operation of the spatial rectifier 10. Often, orthotics are designed to be used, for example, while standing. The accelerometer may detect when a user is lying down vertically and may send a signal to deflate the bladder in such a situation. A temperature sensor can be added to monitor the air temperature in which the pressure sensor and/or mechanical pump are operated. A solenoid valve can be added to electronically change the state of a valve, such as the release valve 30. Multiple air bladders 12 can be used to form zones that provide differential tilt and expansion of the support materials 14, 16. The use of multiple air bladders 12 may be determined by the application—including the size and shape of the void(s) to be filled.

The present invention could be made to operate in the same or similar manner by using one support material instead of two. The use of a single support material may be disposed between the bladder 12 and the body of the user. To limit the expansion of the bladder 12, a strap could be mounted to the support layer at two points and pulled across the bladder 12.

The electronic housing 24 may include other optional features such as an LCD display to give the user additional information. For example, the LCD display may show actual pressure of the air bladder, percent of maximum capacity, angle/degree of tilt to prevent inflation when lying down, and the like.

It should be understood, of course, that the foregoing relates to exemplary embodiments of the invention and that modifications may be made without departing from the spirit and scope of the invention as set forth in the following claims.

What is claimed is:

1. A spatial rectifier comprising:
   at least one flexible support material;
   at least one bladder adjacent to the at least one support material;
   at least one limiter strap to limit expansion of the at least one bladder;
   an air line connected to the at least one bladder, the air line adapted to be connected to an air pump; and
   a pressure sensor adapted to sense a pressure between the bladder and the flexible support material; and a wire harness connecting the pressure sensor to electronic circuitry.

2. A spatial rectifier comprising:
   at least one flexible support material;
   at least one bladder adjacent to the at least one support material;
   at least one limiter strap to limit expansion of the at least one bladder;
   an air line connected to the at least one bladder, the air line adapted to be connected to an air pump;
   an electromechanical pump disposed in a housing, the electromechanical pump adapted to supply air into the bladder via the air line; and
   a solenoid valve disposed in the housing, the solenoid valve adapted to release pressure in the at least one bladder.

3. The spatial rectifier of claim 2, further comprising: a pressure sensor adapted to sense a pressure between the bladder and the flexible support material; and a wire harness connecting the pressure sensor to electronic circuitry, wherein the electronic circuitry is contained within the housing.

4. The spatial rectifier of claim 3, wherein the air line and the wire harness are removably attached to the housing.

5. The spatial rectifier of claim 3, further comprising a battery compartment within the housing, the battery compartment adapted to contain a battery for providing power to the electromechanical pump and the electronic circuitry.

6. A spatial rectifier comprising:
   at least one flexible support material;
   at least one bladder adjacent to the at least one support material;
   at least one limiter strap to limit expansion of the at least one bladder; and an air line connected to the at least one bladder, the air line adapted to be connected to an air pump
   wherein the at least one flexible support material comprises a first support material and a second support material sandwiching the at least one bladder,
   wherein the limiter straps connect the first support material to the second support material; and the limiter straps regulate a maximum spacing between the first support material and the second support material.

7. A spatial rectifier comprising:
   at least one flexible support material;
   at least one bladder adjacent to the at least one support material;
   at least one limiter strap to limit expansion of the at least one bladder; and
   an air line connected to the at least one bladder, the air line adapted to be connected to an air pump,
   wherein the at least one flexible support material comprises a first support material and a second support material sandwiching the at least one bladder,
   wherein the bladder is attached to at least one of the first support material and the second support material using a double-sided adhesive tape.

8. A spatial rectifier comprising:
   at least one flexible support material;
   at least one bladder adjacent to the at least one support material;
   at least one limiter strap to limit expansion of the at least one bladder; and
   an air line connected to the at least one bladder, the air line adapted to be connected to an air pump,
   wherein the at least one flexible support material comprises a first support material and a second support material sandwiching the at least one bladder,
   wherein the first support material is positioned on one side of the bladder;
   the second support material is positioned on an opposite side opposite to the one side of the bladder; and
   the second support material is more flexible than the first support material.

9. A spatial rectifier for filling a void between an orthotic and a user, the spatial rectifier comprising:
   a first and a second flexible support material;
   at least one bladder sandwiched between the first and second flexible support materials;
   at least two limiter straps adapted to limit expansion of the at least one bladder;
   an air line connected to the at least one bladder, the air line adapted to be connected to an air pump; and
   a wire harness connected to at least one transducer positioned between the bladder and one of the first and second flexible support materials.

10. The spatial rectifier of claim 9, wherein the transducer is a pressure sensor.

11. The spatial rectifier of claim 10, further comprising a housing, the housing having electronic circuitry housed therewithin, the electronic circuitry adapted to receive a signal from the pressure sensor.

12. The spatial rectifier of claim 11, further comprising an electromechanical pump housed within the housing, the air line operatively connected to the electromechanical pump, wherein the pressure sensor controls operation of the electromechanical pump.

13. The spatial rectifier of claim 9, wherein: the first support material is positioned on one side of the bladder; the second support material is positioned on an opposite side opposite to the one side of the bladder; and
   the second support material is more flexible than the first support material.

14. The spatial rectifier of claim 9, wherein the bladder is attached to at least one of the first support material and the second support material using a double-sided adhesive tape.

15. A spatial rectifier for filling a void between an orthotic and a user, the spatial rectifier comprising:
- a first and a second flexible support material;
- at least one bladder sandwiched between the first and second flexible support materials; at least two limiter straps adapted to limit expansion of the at least one bladder; and
- an air line connected to the at least one bladder, the air line adapted to be connected to an air pump, wherein the first support material is positioned on one side of the bladder; the second support material is positioned on an opposite side to the one side of the bladder; and
- the second support material is more flexible than the first support material.

16. The spatial rectifier of claim 15, further comprising:
- a wire harness connected to at least one pressure sensor positioned between the bladder and one of the first and second flexible support materials;
- a housing, the housing having electronic circuitry housed therewithin, the electronic circuitry adapted to receive a signal from the pressure sensor; and
- an electromechanical pump housed within the housing, the air line operatively connected to the electromechanical pump, wherein the pressure sensor controls operation of the electromechanical pump.

17. The spatial rectifier of claim 15, wherein the bladder is attached to at least one of the first support material and the second support material using a double-sided adhesive tape.

\* \* \* \* \*